US005350673A

United States Patent [19]
Campbell et al.

[11] Patent Number: 5,350,673
[45] Date of Patent: * Sep. 27, 1994

[54] DETECTION OF A UNIQUE CHLAMYDIA STRAIN ASSOCIATED WITH ACUTE RESPIRATORY DISEASE

[75] Inventors: Lee A. Campbell; Chou-chou Kuo; J. Thomas Grayston, all of Seattle, Wash.

[73] Assignee: Washington Research Foundation, Seattle, Wash.

[*] Notice: The portion of the term of this patent subsequent to Jan. 25, 2011 has been disclaimed.

[21] Appl. No.: 186,198

[22] Filed: Jan. 24, 1994

Related U.S. Application Data

[63] Continuation of Ser. No. 946,821, Sep. 16, 1992, Pat. No. 5,281,518, which is a continuation of Ser. No. 746,053, Aug. 12, 1991, abandoned, which is a continuation of Ser. No. 488,524, Feb. 28, 1990, abandoned, which is a continuation of Ser. No. 71,691, Jul. 9, 1987, abandoned, which is a continuation-in-part of Ser. No. 858,380, May 1, 1986, abandoned.

[51] Int. Cl.$^5$ ............................................. C12Q 1/68
[52] U.S. Cl. ................................... 435/6; 435/317.1; 435/820; 436/501; 536/23.1; 536/23.7; 536/24.32
[58] Field of Search ................. 435/6, 91, 317.1, 820; 436/501, 808; 536/23.7, 23.1, 24.32, 25.32

[56] References Cited

U.S. PATENT DOCUMENTS

| | | | |
|---|---|---|---|
| 4,407,943 | 10/1983 | Cole et al. | 435/7 |
| 4,497,899 | 2/1985 | Armstrong et al. | 436/510 |
| 4,582,791 | 4/1986 | Khanna et al. | 435/7 |
| 4,731,458 | 3/1988 | Palva et al. | 435/6 |
| 4,755,458 | 7/1988 | Rabbani et al. | 435/5 |
| 5,008,186 | 4/1991 | Grayston et al. | 435/7 |
| 5,281,518 | 1/1994 | Campbell et al. | 435/6 |

FOREIGN PATENT DOCUMENTS

| | | |
|---|---|---|
| 124124 | 11/1984 | European Pat. Off. |
| 2156074 | 10/1985 | United Kingdom |
| 8502685 | 6/1985 | World Int. Prop. O. |
| 8602355 | 4/1986 | World Int. Prop. O. |

OTHER PUBLICATIONS

Kuo et al., "Primary Isolation of TRIC Organisms in HeLa 229 Cells Treated with DEAE-Dextran", *J. Infect. Disc.*, 125(6): 665–668 (Jun., 1972).

Dwyer et al., "Chlamydial Infection, Results of Micro-immunofluorescence Tests for the Detection of Type-specific Antibody in Certain Chlamydial Infections" *Brit F. Verner. Dis.* 48:452–459 (1972).

Stephens et al., "Monoclonal Antibodies to *Chlamydia trachomatis*" *J. Immunol.* 128(3): 1083–1089 (Mar., 1982).

Saikku et al., "Serological Studies in Chlamydial Pneumonias", *5th Int'l. Symposium on Human Chylamydial Infections*, Lund, (Jun. 15–19, 1982).

Burney et al., "The Epidemiology of Chlamydial Infections in Childhood: A Serological Investigation" *Int'l J. of Epidemiol.* 13:491–495 (1984).

Grayston et al., "Seroepidemiology with TWAR a New Group of *Chlamydia psittaci*" *ICAAC* Abst. 290:1126 (1984).

Hyypia et al., "Analysis and Detection of Chlamydial DNA", *J. Gen. Microbiol.* 130: 3159–3164 (1984).

Saikku et al., "An Epidemic of Mild Pneumonia Due to an Unusual Strain of Chlamydia psittaci" *J. Infect. Dis.* 151:832–839 (May, 1985).

Stephens et al. "Molecular Cloning and Expression of *Chlamydia trachomatis* Major Outer Membrane Protein Antigens in Escherichia coli "*Infect. Immun.* pp. 713–718 (1985).

Grayston et al., "Isolation of TWAR Strains, a 'Human' *Chlamydia psittaci*" *ICAAC* Abst. 257:899 (1985).

Marrie et al., "Chlamydia Pneumonia" *ICAAC* Abst. 252:864 (1985).

Wang et al., "Immunotyping of *Chlamydia trachomatis* with Monoclonal Antibodies" *J. Infect. Des.* 152(4): 791–800 (1985).

(List continued on next page.)

*Primary Examiner*—Christine M. Nucker
*Assistant Examiner*—Laurie Scheiner
*Attorney, Agent, or Firm*—Townsend and Townsend Khourie and Crew

[57] ABSTRACT

Methods for detecting a unique strain of Chlamydia associated with acute respiratory disease are disclosed. These methods utilize monoclonal antibody directed against an antigenic determinant of the TWAR organism, or DNA probes capable of specifically hybridizing to at least a portion of the DNA sequence of the TWAR organism. A method for determining the presence of antibodies to the TWAR organism, utilizing elementary bodies of the TWAR organism as antigen is also disclosed.

9 Claims, 2 Drawing Sheets

OTHER PUBLICATIONS

Grayston et al., "A New *Chlamydia psittaci* Strain, TWAR, Isolated in Acute Respiratory Tract Infections" *N. Eng. J. Med.* 315:161–168 (Jul. 17, 1986).

Forsey et al., "Prevalence in Human Beings of Antibodies to Chlamydia IOL-207, an Atypical Strain of Chlamydia" *J. Infect.* 12:145–152 (1986).

Schachter, "Human Chlamydia Psittaci Infection", Proceedings of the 6th International Symposium on Human Chlamydial Infections Cambridge University Press, Cambridge, pp. 311–320 (1986).

Kuo et al., "Identification of a New Group of *Chlamydia psittaci* Strains called TWAR" *J. Clin. Micro.* 24:1034–103 (Dec., 1986).

Campbell, Kuo and Grayston, "DNA Analysis of a New Chlamydia Agent (TWAR) Associated with Acute Respiratory Disease," *Abstr. ASM Ann. Mtg.* (1987).

 
FIG. 1A.  FIG. 1B.
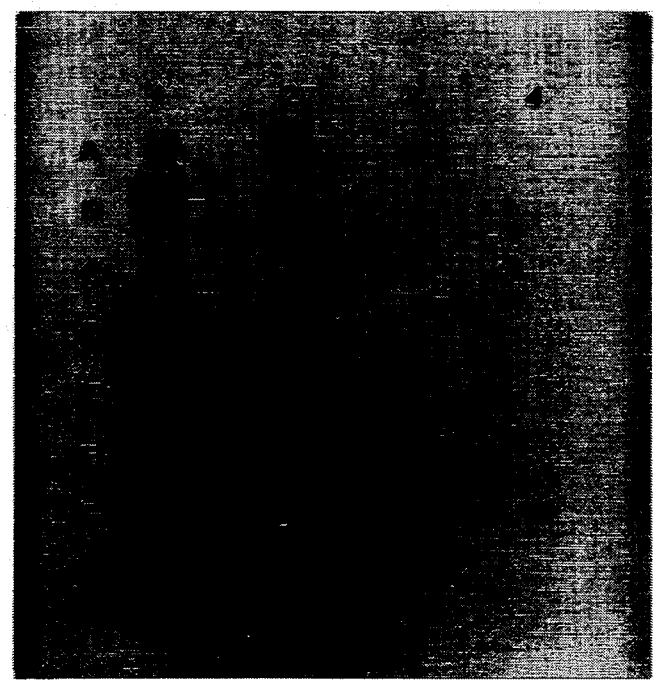
FIG. 2.

DETECTION OF A UNIQUE CHLAMYDIA STRAIN ASSOCIATED WITH ACUTE RESPIRATORY DISEASE

This invention was made with government support under grant number AI 16222 and AI 21885 awarded by the National Institutes of Health. The government has certain rights in the invention.

RELATED APPLICATIONS

This application is a continuation of U.S. Ser. No. 07/946,821, filed Sep. 16, 1992 now U.S. Pat. No. 5,281,518, which is a continuation of U.S. Ser. No. 07/746,053, filed Aug. 12, 1991, abandoned, which is a continuation of U.S. Ser. No. 07/488,524, filed Feb. 28, 1990, abandoned, which is a continuation of U.S. Ser. No. 07/071,691, filed Jul. 9, 1987, abandoned, which is a continuation-in-part of U.S. Ser. No. 06/858,380, filed May 1, 1986, abandoned.

TECHNICAL FIELD

The present invention relates to the detection of Chlamydia strains in general, and more specifically, to the use of monoclonal antibodies and DNA probes in the detection of a unique Chlamydia strain associated with respiratory infection.

BACKGROUND ART

Chlamydia are obligate intracellular parasites that are ubiquitous throughout the animal kingdom and are known to cause a variety of diseases. The Chlamydia genus has two recognized species, *C. trachomatis* and *C. psittaci*, with further differentiation of *C. trachomatis* into three biovars. *C. trachomatis*, the species that is a primary human pathogan, causes ocular, respiratory, and ufogenital infections. *C. trachomatis* can initially colonize the mucous membranes, including the conjunctiva, nasopharynx, rectum, urethra, and cervix, after which the infection may spread to affect the deeper organ systems.

The other species of Chlamydia, *C. psittaci*, is responsible for the human respiratory disease, psittacosis. Psittacosis is usually contracted by exposure to infected birds, outbreaks of psittacosis having occurred in association with turkey and duck processing plants and among pet shop clientele. The disease often resembles atypical pneumonia and may range in severity from mild to fatal. Although epidemics of such pneumonia have usually been traced to infected birds, an avian vector is not always found. For instance, during a radiographic survey in northern Finland in 1978, an epidemic of mild pneumonia was found in two communities; however, arian transmission was not detected.

Seroepidemiological studies have implicated an unusual strain of Chlamydia in this and several other pneumonia epidemics in northern Europe. This new strain of Chlamydia has more recently been established as an important respiratory pathogan, being responsible for perhaps up to 12% of the atypical pneumonia cases in adult populations studied. However, most infections have been inadequately treated with antibiotics due to a mistaken belief that the causative agent was *Mycoplasma pneumonias* or influenza virus A or B. While antibiotic treatment with erythromycin in the low doses used for *M. pneumoniae* is effective against Mycoplasma infection, erythromycin at this dose is not effective against chlamydial infections. Further, these infections are often characterized by a relapsing illness after an apparent resolution of symptoms.

In light of this association between a new strain of Chlamydia and acute respiratory disease, it would be highly desirable to provide an accurate and cost-effective method for diagnosing the presence of this new strain, thereby permitting an effective antibiotic treatment of the primary infection. The present invention provides such a method and is further characterized by other related advantages.

DISCLOSURE OF THE INVENTION

Briefly stated, the present invention provides methods for detecting the presence of a TWAR organism of Chlamydia in biological samples. These methods utilize either a monoclonal antibody directed against an antigenic determinant of the TWAR organism or DNA probes specific for the TWAR organism.

In one aspect of the invention, the method comprises the steps of (a) exposing a biological sample suspected of containing the TWAR organism to a labeled monoclonal antibody directed against an antigenie determinant of the TWAR organism; and (b) detecting the presence of immunocomplexes formed between the monoclonal antibody and the TWAR organism.

A related method for detecting the presence of the TWAR organism comprises (a) combining a biological sample suspected of containing the TWAR organism with HeLa cells such that the TWAR organism becomes intracellular; (b) incubating the HeLa cells containing the TWAR organism; (c) exposing the HeLa cells/TWAR organism to a labeled monoclonal antibody directed against an-antigenic determinant of the TWAR organism; and (d) detecting the presence of immunocomplexes formed between the TWAR organism and the labeled monoclonal antibody. In a particularly preferred embodiment of the present invention, the step of combining comprises inoculating the HeLa cells with the sample and subsequently centrifuging the inoculated sample onto the HeLa cells. It is also preferable to pratrear the HeLa cells with DEAE-dextran and cyclohexamide.

A third aspect of the present invention discloses a method for determining the presence of antibodies to the TWAR organism of Chlamydia in a biological sample. The method generally comprises (a) incubating the biological sample with elementary bodies of the TWAR organism to form a reaction mixture; and (b) analyzing the reaction mixture to determine the presence of antibodies to the TWAR organism. In a preferred embodiment, the step of analyzing comprises contacting the reaction mixture with a labeled specific binding partner for the antibody and detecting the label. In this regard, the specific binding partner may be goat anti-human IgM or goat anti-human IgG.

In all of the methods briefly described above, the monoclonal antibody may be labeled with an enzyme, fluorophore, radioisotope, or luminescer. In this regard, the step of detection would normally be by enzyme reaction, fluorescence, radioactivity, or luminescence emission, respectively.

The methods described above may be applied to a variety of biological samples in order to detect the presence of the TWAR organism or antibodies to the TWAR organism. Bodily secretions, bodily fluids, and tissue specimens are all suitable samples. Examples of bodily secretions include cervical secretions, trachialbronchial secretions, and pharyngeal secretions. Suitable bodily fluids include blood, tears, and central nervous system fluid. Examples of tissue specimens include a variety of biopsies, such as a biopsy of lung tissue or fallopian tube tissue. In addition, tissue from substantially all areas may be examined within a postmortem examination, including heart tissue and lung-tissue.

In accordance with the present invention, continuous hybrid cell lines are established that produce monoclonal antibodies directed against an antigenic determinant of the TWAR organism for use in the methods described above. In a particularly preferred embodiment, the cell line comprises the hybridoma clone RR 402 or TT 205. Monoclonal antibodies produced by such cell lines are also disclosed.

As noted above, the present invention also discloses DNA probes specific for the TWAR organism. The probes may be used within methods for detecting the presence of the TWAR organism in biological samples containing at least a portion of the DNA sequence of the TWAR organism.

In one aspect of the present invention, the method comprises the steps of (a) treating a biological sample suspected of containing the TWAR organism to isolate the DNA associated with the sample; (b) affixing the isolated DNA to a substrate; (c) incubating the substrate bearing DNA with a labeled DNA probe capable of specifically hybridizing to at least a portion of the DNA sequence of the TWAR organism; (d) separating nonhybridized probe from the substrate; and (e) detecting the amount of label associated with the substrate, and therefrom determining the presence or absence of the TWAR organism.

Within another aspect of the present invention, the method comprises (a) affixing a biological sample suspected of containing the TWAR organism to a substrate; (b) treating the substrate bearing the affixed sample to expose the DNA associated with the sample; (c) incubating the substrate bearing DNA with a labeled DNA probe capable of specifically hybridizing to at least a portion of the DNA sequence of the TWAR organism; (d) separating nonhybridized probe from the substrate; and (e) detecting the amount of label associated with the substrate and therefrom determining the presence or absence of the TWAR organism.

Within the methods described above, the probe may be a whole chromosomal DNA probe or a DNA fragment probe derived from the TWAR organism, These and other aspects of the present invention will become evident upon reference to the following detailed description and attached drawings.

BRIEF DESCRIPTION OF THE DRAWINGS

FIG. 1A is a photomicrograph demonstrating TWAR inclusions morphologically typical of C. psittaci.

FIG. 1B is a photomicrograph demonstrating the vacuolar structure typical of C. trachomatis.

FIG. 2 is an autoradiograph of a dot blot of denatured DNA from C. trachomatis, C. psittaci, and TWAR probed with nick-translated whole chromosomal DNA from TWAR isolate AR-39 Lane, 1, A to G: TWAR isolates AR-39 (diluted 5-fold), AR-39 (undiluted), AR-39 (diluted 10-fold), AR-388, AR-231, AR-458, and AR-427, respectively. Lane 2, A and B: TWAR isolates LR-65 and TW-183, respectively. Lane 2, C to E: C. trachomatis serovars L2, B, and D, respectively. Lane 3, A to C, E and F: C. psittaci 6BC, GPIC, Mn, FP, and OA, respectively. Lane 4, A to D: HeLa DNA diluted 2-fold, 4-fold, 10-fold, and 100-fold, respectively.

BEST MODE FOR CARRYING OUT THE INVENTION

Figure 3A:
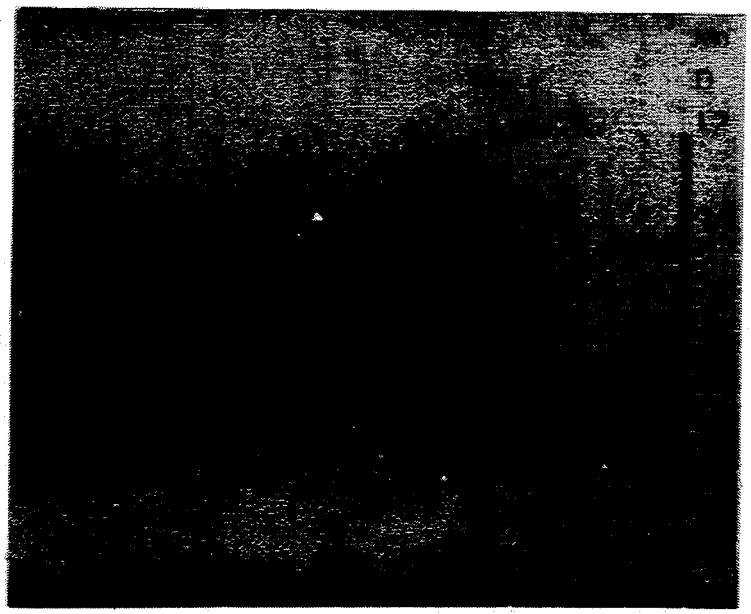
FIG. 3A is an autoradiograph of a Southern hybridization of Msp I digested DNA probed with a 3.8 kbp Pst 1 fragment isolated from a gene bank of TWAR strain AR-39 DNA.

As noted above, seroepidemiological studies have implicated an unusual strain of Chlamydia in several pneumonia epidemics in northern Europe and elsewhere. This new strain of Chlamydia is herein referred to as "TWAR," from the laboratory designations of the first two isolates (TW-183 and AR-39 ). TWAR has been shown to belong to the genus Chlamydia, but may be differentiated from C. trachomatis and C. psittaci by several criteria. With respect to inclusion morphology and presence of glycogen in inclusions, TWAR inclusions are more closely related to C. psittaci based upon their oval and dense appearance and absence of glycogen, in contrast to the vacuolar nature of C. trachomatis inclusions which contain glycogen. In addition, the TWAR organism does not react with C. trachomatis species-specific monoclonal antibody (Stephens et al. , J. Immunol. 128: 1083, 1982).

While the TWAR organism clearly does not belong to the C. trachomatis species, it also exhibits important differences from currently recognized C. psittaci strains. TWAR and the other C. psittaci strains are immunologically distinct; no cross-reactions with the other C. psittaci strains have been found. Further, in the production of monoclonal antibodies against the TWAR organism (more thoroughly described below) , no C. psittaci species-specific antibodies were detected, only genus- and strain- (TWAR serovar) specific antibodies were found. It is also interesting to note that while a plasmid has been found in almost all C. psittaci and C. trachomatis chlamydial strains examined, the TWAR organism has no plasmid. In addition, while all known C. psittaci strains have an animal or bird host, no animal or bird host for the TWAR organism has been found. In accordance with the present invention, the TWAR organism is therefore defined to include any Chlamydia strain that is morphologically similar to but distinct from C. psittaci, and immunologically distinct from currently recognized C. psittaci strains. A representative TWAR strain (AR-39) has been deposited with the American-type culture collection and assigned accession number 53592.

Hybridoma formation and production of monoclonal antibodies have been shown to be useful in immunodiagnosis of a variety of microbiological diseases. More specifically, monoclonal antibodies allow detection and serological classification of human infections. In addition, these monoclonal antibodies facilitate identification of genus- and species-specific antigens.

As noted above, continuous hybrid cell lines are established which are capable of producing monoclonal antibodies to an antigenic determinant of the TWAR organism. A general protocol for establishing such cell lines includes immunizing an experimental animal, usually a mouse, with an appropriate antigen. Immune spleen cells are then isolated and fused with myeloma or lymphoma cells by exposure to a chemical agent, such as polyethylene glycol. Fused hybrid cells are then incubated in a selective medium, such as HAT medium, that precludes the growth of the malignant cell line. Hybridoma cells are cloned by limiting dilution, and culture supernatants are assayed for secretion of monoclonal antibody having a desired specificity. Large yields of selected monoclonal antibodies may be obtained through ascitic growth of hybridomas in vivo.

In order to obtain monoclonal antibodies that are specific for the TWAR organism, an appropriate TWAR antigen must be prepared. TWAR isolates may be cultured from throat (oropharynx) specimens of patients, either through eukaryotic cell culture or embryohated egg yolk sac culture. Most primary isolates require egg-adaptation of the TWAR organism prior to successful eukaryotic cell culture. In particular, it may be preferable to passage the TWAR isolates once or twice in yolk sac culture and then inoculate them onto cultures of HeLa 229 cells propagated in vials. It is also preferable to pretreat the HeLa cells with DEAE-dextran and cyclohexamide. The TWAR isolates may be adapted to grow in cell culture by repeated culture passages. In particular, approximately 10 or more serial culture passages may be advantageous for adaptation to HeLa cell growth.

Referring now to FIGS. 1A and 1B, photomicrographs are presented showing a HeLa 229 cell monolayer infected with a TWAR organism and a *C. trachomatis*, respectively. FIG. 1A demonstrates TWAR inclusions morphologically typical of *C. psittaci*. The TWAR infection exhibits relatively dense cytoplasmic inclusions that have not indented or displaced the nucleus. In contrast, FIG. 1B demonstrates typical vacuolar inclusions of *C. trachomatis* that indent the nucleus.

The infected cell cultures are normally monitored for TWAR organism infectivity; and when a certain percentage of cells are infected, multiple vial cultures are inoculated in preparation for growth in large culture bottles. In a preferred embodiment, when 50% infectivity is obtained, 20 to 30 vials of HeLa 229 cells may be infected to provide the inoculum for a 32-oz prescription bottle culture. Subsequent serial pasages will increase the number of TWAR strain Chlamydia. This adaptation and scale-up will yield a sufficient quantity of TWAR antigen for monoclonal antibody production and screening.

The immunogen for hybridoma production employed within the present invention was purified TWAR antigen. In a preferred embodiment, the antigen is Renografin-purified TWAR elementary bodies (>99% purified). Hybridomas may be prepared by fusion of immune mouse spleen cells with NS-0 myeloma cells, and hybridoma clones secreting antichlamydial antibodies identified. In a preferred embodiment, hybridoma culture supernatants are screened by ELISA. In a particularly preferred embodiment, the ELISA employs peroxidase-conjugated anti-mouse immunoglobulins and a colorimetric detection system. Further testing of monoclonal antibody specificity by a micro-immunofluorescence technique (S. P. Wang and J. T. Grayston, *Amer. J. Ophthal.* 70: 3678, 1970) is also preferred.

TWAR-elicited hybridomas may be intraperitoneally inoculated into syngeneic BALB/c mice. It is preferable to Pristane-prime the mice 2 weeks prior to inoculation. The resultant ascites fluid may be harvested, and monoclonal antibodies purified. In a preferred embodiment, ascitic monoclonal antibodies are affinity purified on a protein-A-sepharose column.

Selected TWAR monoclonal antibodies may be labeled for use within the methods described herein. Preferred labels include enzymes, fluorophores, radioisotopes, and luminescers. These and other labels are well known in the art. A particularly preferred label in this regard is fluorescein. The labeled TWAR monoclonal antibodies may then be examined for genus-, species- and strain-specificity. As shown in Table 1, when employed in a micro-immunofluorescence assay, the TWAR-elicited monoclonal antibodies reacted with TWAR isolates, but not *C. trachomatis* or *C. psittaci.*

TABLE 1

Specificity of TWAR-Elicited Monoclonal Antibodies

| Chlamydial Strains | Micro-IF Antibody Titer with TWAR-Elicited MAb | ELISA Antibody Titer with Genus-Specific MAb |
|---|---|---|
| TWAR - TW 183 | 6400 | 3200 |
| AR 39 | 6400 | 3200 |
| AR 277 | 6400 | 3200 |
| AR 388 | 6400 | 3200 |
| *C. psittaci* (6 strains) | 0 | 3200 |
| *C. trachomatis* (15 serovars) | 0 | 3200 |

Fluoroscein-conjugated TWAR monoclonal antibodies specifically stained TWAR elementary bodies and TWAR inclusion in infected cultured cells, but did not stain other Chlamydia. The present invention thus provides a monoclonal antibody that binds to a TWAR-specific antigenic determinant.

Within the present invention, a TWAR-specific monoclonal antibody has been employed in diagnostic assays of biological specimens. In particular, the present invention provides methods for detecting TWAR organisms in smears of clinical specimens and in inoculated cell cultures. These methods utilize labeled TWAR-specific monoclonal antibody that binds directly to TWAR-specific antigenic determinants in immobilized specimens. The specimens may be immobilized on a solid support, such as a glass slide, coverslip, or a microtiter well. The specimen or biological sample should also be fixed to the solid support, as by methanol or ethanol fixation. After the sample is fixed or bound to the surface, the sample is exposed to the labeled monoclonal antibody. Alternatively, a labeled second antibody capable of binding to the TWAR-specific monoclonal antibody may be employed. This modification of the method may provide an enhancement in the signal of the label. Identification of TWAR organisms in smear specimens by a direct fluorescent antibody technique is rapid, simple, and relatively inexpensive. The smear technique can be used both in clinical settings (early diagnosis, improved opportunity for isolation of the causative organism, follow-up on success of treatment) and in epidemiological settings.

In addition to providing a method for detecting the presence of the TWAR organism, the present invention provides a method for determining the presence of antibodies to the TWAR organism in biological samples. A particularly preferred embodiment for the screening of serum or bodily fluids for TWAR antibodies is the micro-IF assay. Typically, antigen (Chlamydia elementary body antigen) is fixed onto a microscopic slide, and the slide incubated with a sample suspected of containing TWAR antibody. A labeled specific binding partner is then added (such as fluorescein-conjugated anti-mouse immunoglobulin) and the reaction observed to determine the presence of antibodies to the TWAR organism.

The use of DNA probes has also been shown to be useful in the diagnosis of a variety of microbiological diseases. More specifically, DNA probes can be used to detect purified DNA, to detect unpurified DNA in isolated colonies, or to detect DNA directly in tissues, body fluids, foods, and water. One advantage of the use of DNA probes is that the organism can be detected in the presence of coexisting antibody that may prevent immunological detection through the masking of critical binding sites. Moreover, DNA probes have the potential to be used on samples not readily assayed by immunofluorescent techniques. Several different approaches have been used in the development of DNA probes specific for a particular patbogen. These approaches include: (a) whole chromosomal DNA; (b) sequences associated with a virulence function unique to that pathogen; (c) plasmid DNA; (d) ribosomal RNA genes; and (e) cloned, random sequences specific for the organism.

However, since TWAR does not contain plasmid DNA and since virulence factors have not been identified for this organism, the present invention discloses both a whole chromosomal DNA probe and representative cloned fragments of TWAR DNA that are specific for the TWAR organism. The use of these probes permits differentiation of TWAR from *C. trachomatis*, as well as from *C. psittaci*.

As described in more detail below, the DNA probes were selected by virtue of their ability to hybridize with TWAR DNA sequences, and their lack of hybridization with DNA from *C. trachomatis* and *C. psittaci*.

Briefly, for the whole chromosomal DNA probes, TWAR DNA was isolated from purified elementary bodies, nick-translated, and used as a probe in a dot blot hybridization. As shown in FIG. 2, the whole chromosomal DNA probe may be used to identify and differentiate the TWAR organism from *C. trachomatis* and *C. psittaci*.

Briefly, for the DNA fragment probes, the TWAR strains were isolated from a suitable biological sample and the DNA purified. After restriction endonuclease digestion, the mixture of DNA fragments was separated by agerose gel electrophoresis. The DNA fragments were then transferred by either blotting or electroelution to nitrocellulose paper. Hybridization probes were then added to detect homologous sequences. More specifically, five random, cloned, TWAR Pst I DNA fragments having approximate sizes of 500 bp, 900 bp, 1200 bp, 3200 bp, and 3800 bp were purified from a gene bank of AR-39 DNA and used for probing chromosomal digests. As shown in FIG. 3, the hybridizing fragment(s) in each case was the same for all TWAR isolates. In addition, the probes were TWAR-specific, as no activity was observed with the *C. trachomatis* or *C. psittaci*.

Figure 4:
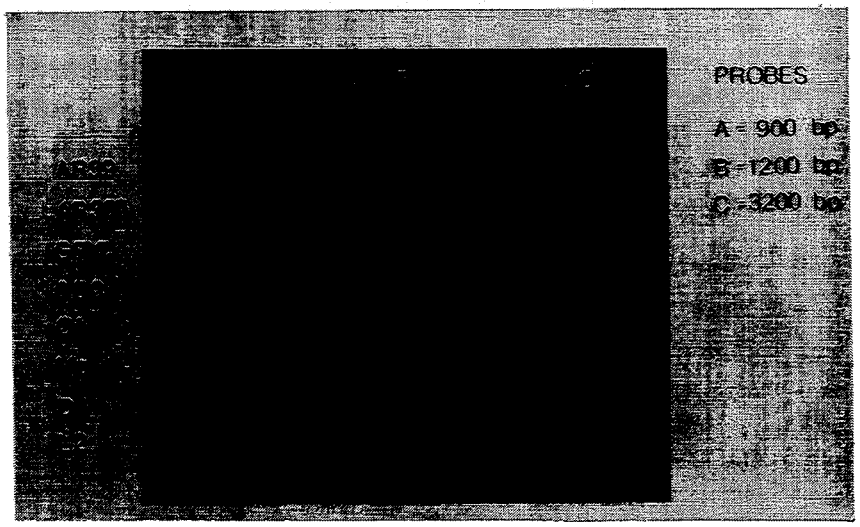
FIG. 4 is an autoradiograph of a dot blot of denatured whole chromosomal DNA from TWAR, C. psittaci, and C. trachomatis probed with three TWAR-specific DNA probes isolated and purified from a gene bank consisting of TWAR DNA digested with Pst I.

For use in clinical applications, cloned and purified TWAR fragments may be used as probes in a dot blot hybridization. As shown in FIG. 4, when lysed elementary bodies of TWAR, *C. psittaci* and *C. trachomatis* were tested, the fragments reacted only with TWAR. Briefly, for either type of probe, a biological sample from a patient suspected of containing the infectious agent is disrupted to release its DNA, and the DNA bound in a spot on nitrocellulose by a combination of physical (heating) and chemical (salts, detergents) means. The method of sample preparation prior to application to nitrocellulose will depend on the sample source. In all cases, the nitrocellulose is preincubated in 1M ammonium acetate to increase binding of the DNA. In order to process and concentrate large numbers of samples, the samples are applied to nitrocellulose, preferably by the use of an apparatus, such as a BioDot Microfiltration apparatus. If the DNA has been isolated previously, the samples are boiled for 10 minutes in 0.3M NaCl and 2M cold ammonium acetate added. One-hundred $\mu$/ml samples are applied to the dot blot apparatus and filtered through under vacuum. Wells are washed with 2M ammonium acetate to remove any residual nucleic acid bound to the well. When the sample to be tested consists of EBs or cultured bacteria, cultures are lysed and chromosomal DNA denatured by boiling in 0.5 N NaOH for 10 minutes, neutralized by the addition of HCl to a final concentration of 0.5 N HCl, and brought to a final concentration of 6×SSC. For clinical respiratory tract specimens, samples are treated with proteinase K, solubilized by the addition of SDS, extracted with phenol, RNase treated, phenol chloroform extracted, and ethanol precipitated. The samples are then denatured by boiling as described above. Following sample appliestion, the filter is incubated at 80° C. for 2 hours, prehybridized for 2–4 hours, and hybridized by standard methods (Maniatis et al., Molecular Cloning: A Laboratory Manual, Cold Spring Harbor Laboratory, 1983).

It will be evident to one skilled in the art that the methods briefly described above are merely representative of suitable methods for sample preparation. In essence, the purpose of sample preparation is to liberate the DNA associated with the sample and affix the DNA to a substrate, such as nitrocellulose, either before or after liberation. These methods may be used to prepare both whole chromosomal DNA probes or DNA fragment probes.

If there is complementary DNA from the patient's sample, the labeled hybridization probe will be bound; if there is no complementary DNA on the spot, the hybridization probe will not be bound and can easily be washed away. If a non-radioactive probe is used, a substrate to the label on the hybridization probe may be necessary in order for the reaction to be measured If the label is $^{32}$p the measurement involves the development of photographic film. If the label is an enzyme, the measurement may be either by densitometry or by direct visualization.

In order to determine the sensitivity of selected DNA probes, different dilutions of predetermined concentrations of TWAR may be lysed and applied to nitrocellulose by filtration, as described above. Particle counts of TWAR may be done by negative staining with congo red (Gerloff et al., *J. Infect. Dis.* 123: 429–432, 1971) or by electronmicroscopy (Wang et al., *Am. J. Opthal.* 1443–1454, 1967).

One advantage of the TWAR-specific fragments described herein over the whole chromosomal DNA probe is their purity. The minor contamination of the chlamydial chromosomal DNA with cell culture DNA may result in a slight nonspecific background reaction.

To circumvent this potential problem, whole chromosomal DNA may be prepared from TWAR organisms grown in McCoy cells or other non-human cell lines that adequately support TWAR growth. Additional assets of the cloned fragments are the ease and decreased cost of isolating large quantities of these specific sequences in comparison to growing large quantities of the TWAR organisms for isolation of whole chromosomal DNA. In addition to the methods described herein for the isolation of DNA probes, the sensitivity of DNA probes may be improved by various means, for example through (a) the use of a single-strand probe and (b) the isolation of ribosomal rRNA genes.

The following examples are offered by way of illustration, and not by way of limitation.

EXAMPLE 1

Growth and Isolation of TWAR Organisms

A. Cell Culture Isolation

Specimens of throat (oropharynx) swabs in transport media (sucrose/potassium/glutamate; SPG) from patients with acute respiratory disease were cultured according to a method modified from C. C. Kuo etal. (*J. Infect. Dis.* 125: 665–668, 1972). Each specimen was inoculated onto three vials containing HeLa 229 cell monolayers which had been pretreated with DEAE-dextran (30 Mg/ml) prior to inoculation. The inoculum was centrifuged onto the cells at 2,200 rpm for 60 minutes at room temperature. The vials were than incubated with medium containing cycloheximide (0.5–0.8 μl/ml) at 35° C. for 72 hours. The monolayer from one of the vials was fixed with methanol and stained with fluorescent antibody to search for inclusions indicative of infection. The other two vials were available to provide inoculum for a second passage.

B. Egg Culture Isolation

Specimens of throat (oropharynx) swabs in SPG transport media from patients with acute respiratory disease were inoculated into the yolk sac of embryohated eggs, 6 to 8 days of age, according to the method of J. T. Grayston etal. (*Proc. Soc. Exp. Biol. Med.* 103: 596, 1960). Streptomycin was added to the specimen until a concentration was reached that gave 10 mg per egg on inoculation. The eggs were incubated at 35° C. and candled daily. Upon death, or survival for 12 to 13 days, yolk sacs were harvested and stained by a modified Macchiavello staining method to look for elementary bodies of Chlamydia. When TWAR monoclonal antibody conjugated to fluorescein became available for staining the infected yolk sacs, the TWAR organisms could be seen much more readily. Several passages previously considered negative by Macchiavello staining were found to contain the TWAR organism. Positive cultures usually demonstrated increased numbers of elementary bodies on subsequent passage.

C. Adaptation of TWAR Strains to Grow in Cell Cultures

All but one of the 13 TWAR isolates so far obtained required original inoculation in the yolk sac of embryohated eggs, with egg adaptation of the organisms (one or two passages) prior to cell culture inoculation to successfully adapt most of the TWAR isolates to HeLa 229 cell culture vials.

Serial passages of TWAR organisms were carried out in vial cultures of HeLa 229 cells, modified from the method of Kuo et al. (in "Nongonococcal Urethritis and Related Infections," pp. 328–336, 1977). As described for cell culture isolation (Example 1.A.), three separate HeLa cell monolayers in vials were inoculated for each passage. One was fixed and stained to determine the progress of the infection, and the remaining two monolayers were scraped from the vials and reinoculated exactly as described above for the first passage. At least 10 serial cell culture passages were required for adaptation.

When the infectivity increased so that greater than 50% of the cells were infected, the number of vials inoculated was increased to provide 20 to 30 vials of the infected cells for inoculation into a large culture bottle (32-oz prescription bottle). Serial passages were continued in the bottle culture until 100% of the cells were infected.

EXAMPLE 2

Preparation of TWAR Antigen

Following adaptation of a TWAR strain to 32-oz prescription bottles, the strain was expanded by growth in additional bottles of HeLa 229 cells. The organisms were harvested by rolling the monolayer with glass beads in 20 ml of Hanks balance salt solution. The cells were disrupted by sonication, and the HeLa cell debris was removed by low-speed centrifugation (1,200 rpm for 10 minutes). The organisms were then pelleted by high-speed centrifugation (16,000 rpm for 20 minutes). The TWAR elementary bodies were purified first by cushioning through a 30% Renografin suspension at 16,000 rpm for 40 minutes, which removes approximately 60% of the contaminants and then by passing through a 30% to 65% Renografin linear gradient at 23,00 rpm for 90 minutes. The suspended band of TWAR elementary bodies was more than 99% purified. The method employed was modified from that of R. S. Stephens et al. (*J. Immunol.* 128: 1083, 1982).

EXAMPLE 3

Immunization Schedule

BALB/c mice were immunized with $5\times10^7$ formalinkilled TWAR organisms, intraperitoneally on day 1 and with a similar inoculum intravenously at weekly intervals thereafter for 3 or 4 additional injections. The spleens were harvested 3 days after the last immunization.

EXAMPLE 4

Construction of Hybridomas

The NS-0 myeloma cell line was obtained from Milstein to be used for the fusion procedure. NS-0 cells were routinely grown in RPMI 1640 (GIBCO, Grand Island, N.Y.) containing 15% heat-inactivated fetal calf serum, 1 mM glutamine, and 1 mM pyruvate (referred to as "complete RPMI").

Spleen cell suspensions were prepared by mincing and passing the cells through a fine nylon screen. Lymphocyte cell suspensions were washed three times in serum-free RPMI; the NS-0 cells were washed once in serum-free RPMI.

NS-0 cells and lymphocytes were fused (at a 1:4 ratio or 1:8 ratio) in 40% polyethylene glycol by centrifugation at $250\times G$ for 10 minutes. The cells were washed with 10 vol of complete RMPI and centrifuged at $160\times G$ for minutes. The supernatant was aspirated, and the cells were gently resuspended to $2.5\times10^6$ cells/ml in complete RMPI supplemented with HAT medium (complete RMPI containing $1.0 \times 10^4$ M hypoxanthine, $4.0 \times 10^{-7}$ M aminopterin, and $1.6 \times 10^{-5}$ M thymidine). This hybrid cell suspension was mixed with thymocytes from 3- to 5-week-old BALB/c mice to a final concentration of $2.5 \times 10^6$ thymocytes/ml. The final cell suspension was seeded (in 200 Ml volumes) into the wells of 96-well microtest plates (Costar, Cambridge, Mass.). Additional feedings with HAT medium (50% substitution by volume) were given on days 5 and 8. The continued handling, feeding schedule, and cloning by limiting dilution were performed as described by Stephens et al. (supra).

EXAMPLE 5

Screening of Hybridoma Clones

Anti-chlamydial antibodies in culture fluids were detected by enzyme-linked immunosorbent assay (ELISA). For the antibody assay, $1 \times 10^5$ Chlamydia organisms in 50 µl of phosphate-buffered saline (PBS, pH 7.6) were adsorbed by the individual wells of a microtest plate by incubation overnight at 37° C. Control plates were prepared by allowing uninfected HeLa 229 cells ($10^4$ cells/well) to attach to wells of microtiter plates. The following morning, the wells of the plates were blocked from further nonspecific protein adsorption by a 2-hour incubation with 75 µl of 5% bovine serum albumin (BSA) in PBS. The antibody assay was performed in three steps:

(1) Fifty microliters of culture fluid were incubated in each of the antigen-adsorbed wells for 60 minutes at 37° C. Nonbound immunoglobulins were then removed from the wells by washing three times with PBS containing 1% BSA.

(2) Peroxidase-conjugated anti-mouse immunoglobulins (50 µl) were added to each well and incubated for 60 minutes at 37° C. Residual-unbound peroxidase conjugate was removed by washing three times with PBS.

(3) The immune reactions were detected by adding the substrate o-phenylenediamine and $H_2O_2$, and the color reaction quantitated. Antibody specificity was further determined by testing the culture supernatants that were positive by ELISA in the micro-IF technique (see Example 6).

EXAMPLE 6

Production of Monoclonal Antibodies

Intraperitoneal inoculation of 1 to $5 \times 10^6$ hybrid cells into syngeneic BALB/c mice induced palpable tumors (hybridomas) within 2 to 3, weeks. To assure tumor induction, syngeneic hosts were primed 2 weeks earlier by an intraperitoneal inoculation of 0.5 ml of Pristane (2, 6, 10, 14-tetramethyl pentadecane, Aldrich Chemical Co., Milwaukee, Wis.). In most instances (>90%), the progressive growth of the intraperitoneal transplanted hybridomas was accompanied by production of ascites fluid (1.0 to 5.0 ml/mouse).

Isotypes of the monoclonal antibodies contained in the ascites fluid were determined by ELISA using the MonoAb-Screen system (Zymed Laboratories, San Francisco, Calif.). Before use, ascites fluids were tested for specific antibody activity by the micro-IF technique.

For the micro-IF assay, culture fluids or ascites fluids were reacted with Chlamydia elementary body antigens which were placed on microscope slides for 30 minutes at 37° C. in a moist chamber. After reaction, the slides were washed five times with PBS and air dried. Fluoresceinconjugated anti-mouse immunoglobulins were added and incubated for 30 minutes at 37° C. in a moist chamber. After incubation, the slides were washed five times with distilled water and air dried. A drop of FA mounting fluid was added, and a coverslip was placed on the slide. The reaction was observed under FA-scope. For staining of inclusions, infected HeLa cells were fixed for 10 minutes in absolute methanol and asseyed for TWAR-specific antibody activity.

Monoclonal antibodies contained within ascites fluid were affinity purified on a protein A-Sepharose column (Pharmacia Fine Chemicals, Uppsala, Sweden). Fluorescein isothiocyanate-conjugated monoclonal antibodies were prepared by the method of Goding (J. Immunol. Meth, 13: 215, 1976) and were used at an appropriate dilution as determined by titration for direct immunofluorescence assays. Unconjugated monoclonal antibodies were usually used at 1:100 dilution for indirect immunofluorescence techniques.

EXAMPLE 7

Diagnostic Assay

A. Smear Technique

Monoclonal antibodies to *C. trachomatis* have previously been used for direct fluorescent antibody (FA) assay of smears from clinical specimens. Fluroescein-conjugated monoclonal antibodies specific for TWAR strains have been employed in a similar direct FA assay of respiratory specimens. Briefly, a pharyngeal swab was rolled on a glass slide over two premarked circular areas (5 mm diameter), and the slide was then immersed in 95% ethanol for 10 to 30 minutes. After the slide dried in air, the fluorescent monoclonal antibody conjugate was applied to the specimen area. The slide was incubated at 37° C. for 30 minutes in a moist chamber, washed by briefly dipping through six jars of distilled water, and dried. A drop of Bacto fluorescent antibody mounting fluid (Difco Laboratories, Detroit, Mich.) and a coverslip were applied to the slide, which was then examined under oil immersion at ×500 magnification with an epifluorescence microscope (Carl Zeiss, Oberkochen, West Germany). The entire area of the smear was examined. Findings on slides were considered positive for TWAR strain if at least five fluorescing elementary bodies were found in the specimen. Slides with negative findings were read for 5 minutes, Throat swab smears from six of seven patients with TWAR isolations were stained with fluorescent TWAR monoclonal antibody. In four, typical elementary bodies of Chlamydia were demonstrated.

B. Culture Technique

Fluorescein-conjugated TWAR strain-specific monoclonal antibody was used to identify TWAR isolates in initial HeLa 229 cell culture passage. The cell culture isolation technique is described in Example 1.A. Direct fluorescent antibody (FA) staining with TWAR strain specific monoclonal antibody has greatly facilitated indentification of TWAR isolates and has allowed direct passage of these isolates. Each of the TWAR isolates has been identified in primary HeLa 229 cell culture passage by direct FA staining of inclusions.

C. Serological Technique

TWAR antigens, which were mixed with 3% normal yolk sac homogenate (to assist localization and attachment of the antigens on a slide), were dotted on a microscopic slide, air dried, fixed with acetone for 15 minutes, and air dried. Serial twofold dilutions of serum or bodily fluids (such as tears) were applied onto the antigens and incubated for 30 minutes at 30° C. in a moist chamber. Within this assay, the fluids were reacted with Chlamydia elementary body antigens. After reaction, the slides were washed five times with PBS and air dried. Fluoresceinconjugated anti-mouse immunoglobulins were added and incubated for 30 minutes at 37° C. in a moist chamber. After incubation, the slides were washed five times with distilled water and air dried. A drop of FA mounting fluid was added, and a coverslip was placed on the slide. The reaction was observed under FA-scope. For staining of inclusions, infected HeLa cells were fixed for 10 minutes in absolute methanol and assayed for TWAR-specific antibody activity.

Table 2 illustrates the high frequency of TWAR antibody present in the sera of adults from seven different areas of the world. Further, antibody was found to be present more frequently in males than in females.

TABLE 2

|  | Denmark | Helsinki | Nova Scotia |
|---|---|---|---|
| # Tested | 555 | 271 | 200 |
| | Percent TWAR Antibody | | |
| Male | 48 | 47 | 35 |
| Female | 41 | 36 | 18 |

|  | Taiwan | Japan | Panama | Seattle |
|---|---|---|---|---|
| # Tested | 64 | 196 | 934 | 1042 |
| | Percent TWAR Antibody | | | |
| Male | 59 | 45 | — | 45 |
| Female | 52 | — | 40 | 36 |

EXAMPLE 8

Through characterization of the TWAR DNA, this example demonstrates that the TWAR organism is distinct from C. trachomatis and C. psittaci.

A. Chlamydia strains: Chlamydia strains studied included (1) TWAR: TW-183, AR-39, AR-231, AR-277, AR-388, AR-427, AR-458, and LR-65 (2,3); (2) C. psittaci: 6BC, meningopneumonitis (Mn), feline pneumonitis (FP), guinea pig inclusion conjunctivitis (GPIC), and sheep abortion (OA), and (3) C. trachomatis: B/TW-5/TO, D/UW-3/Cx, and L2/434/Bu. All TWAR strains were pharyngeal isolates obtained from Seattle in 1985, except TW-183, which was isolated from the conjunctiva of a child in Taiwan in 1965. All Chlamydia strains were adapted to grow in HeLa 229 cell cultures and purified through a linear gradient of Renografin.

B. Isolation of Chlamydial DNA: Chlamydial DNA was isolated as previously described for C. trachomatis (Stephens et al., Infect. Immun. 47 : 713–718, 1985). Basically, purified elementary bodies were treated with proteinass K (64 μg/ml) for 1 hr at 37° C. and solubilized in 1% SDS. Following phenol extraction, the aqueous layer was treated with RNase (50 μg/ml) for 30 min at 37° C., extracted with phenol/chloroform, and precipitated with ethanol.

C. Plasmid Screening: None of the eight TWAR isolates examined contained any visible plasmid DNA, as determined by agarose gel electrophoresis, in contrast to the C. trachomatis and C. psittaci controls, which contained a 7.3 and 6.2 kbp plasmid, respectively (Weiss et al., Infect. Immun. 2: 244–248, 1970).

D. Restriction endonuclease analysis and hybridizations: The restriction enzymes used included: Bam HI, BstE II, Dpn I, Eco RI, Hind III, Mbo I, Msp I, Pst I, Sau3A, and Sst I. All techniques were done by standard protocol with hybridizations done under conditions of high stringency (Kingsbury, J. Bacteriol. 98: 1400–1401, 1969). Restriction endonuclease analysis was employed for comparison of TWAR isolates with each other and with strains of the two species of Chlamydia. With each restriction enzyme used, TWAR isolates were readily differentiated from the trachoma and LGV biovars of C. trachomatis and the five different strains of C. psittaci tested. With the limits of resolution of this method, banding patterns of the TWAR isolates were identical with 8 of the enzymes used.

Figure 3B:
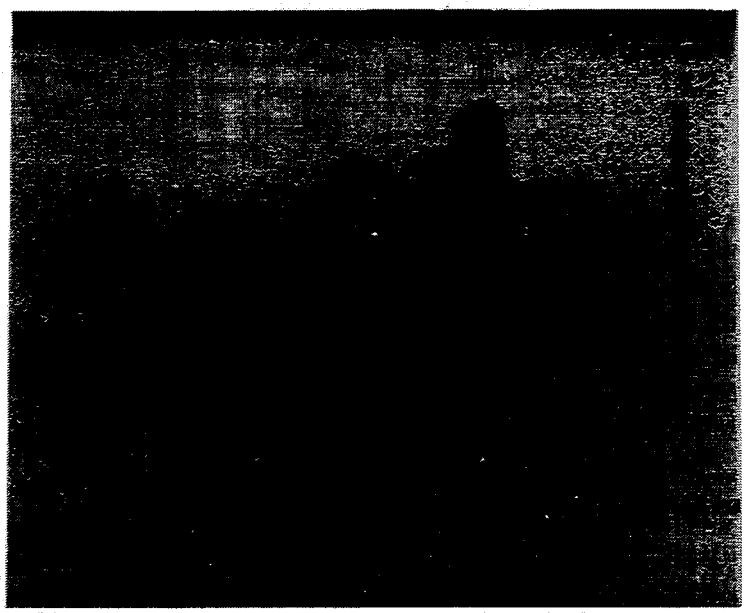
FIG. 3B is an autoradiograph of a Southern hybridization of Hind III digested DNA probed with a 3.2 Pst I fragment isolated from a gene bank of TWAR strain AR-39 DNA.

E. Southern hybridizations: To further investigate the relationship among the TWAR isolates and with the other Chlamydia, five random TWAR DNA fragments having approximate sizes of 500 bp, 900 bp, 1200 bp, 3200 bp, and 3800 bp were purified from a gene bank of AR-39 DNA and used for probing chromosomal digests. As shown in FIG. 3, when the 3.8 kbp (FIG. 3A) TWAR fragment or the 3.2 kbp (FIG. 3B) fragment was used as a probe of Chlamydia DNA digested with Msp I or Hind III, respectively, the hybridizing fragment(s), in each case, was the same for all TWAR isolates. Additionally, both probes were TWAR-specific, as no reactivity was observed with the C. trachomatis or C. psittaci tested. Identical results were obtained with the other 3 probes.

F. DNA Homology Studies Employing Dot Blot Hybridizations Using Whole Chromosomal DNA as a Probe: To determine the relatedness of TWAR to C. trachomatis and C. psittaci, dot blot analyses was employed using whole chromosomal DNA as the probe. Briefly, 0.2–5 μg of purified EB DNA was boiled for 10 minutes in 0.3M NaCl. Subsequently, 2.0M ammonium acetate was added to a final volume of 100 μl Samples were applied to nitroceullose (Trans-Blot, Bio-Rad, Richmond, Calif.) by use of a Bio-Dot Microfiltration apparatus (Bio-Rad, Richmond, Calif). Prior to filtration, the nitrocellulose was washed in 1M ammonium acetate to increase DNA adherence. The nitrocellulose was baked at 80° C. for 2 hours prior and subsequently prehybridized, as described previously. Nick-translated whole chromosomal Chlamydia DNA was denatured by boiling with subsequent quick-cooling and used as the probe in these hybridization experiments. To attempt to roughly quantitate the percent homology, the nitrocellulose was cut into individual dots which were suspended in Omni-fluor (DuPont, Boston, Mass.) for scintillation counting.

In all experiments, HeLa DNA was spotted as a control, as most Chlamydia DNA preparations contain a small amount of HeLa DNA contamination. Whole chromosomal DNA of TWAR strain AR-39, C. trachomatis serovat D, and C. psittaci strains 6BC, FP, OA, and Mn were nick-translated and used as probes of dot blots containing denatured chomosomal DNA of the various isolates. As shown in FIG. 2, neither of the two C. trachomatis biovars nor the 5 C. psittaci strains demonstrated any significant homology to the AR-39 probe. On the other hand, all TWAR isolates gave strong hybridization signals. Analogous results were obtained when TW-183 was used as the probe. when the reciprocal experiments were done using C. trachomatis or C. psittaci DNA as the probe, no reactivity above background was observed with any of the TWAR isolates (data not shown).

EXAMPLE 9

Assays utilizing TWAR-specific probes: As described above, and as shown in FIG. 4, when cloned, purified, TWAR fragments were used as probes in dot blots of lysed elementary bodies of TWAR, *C. psittaci*, and *C. trachomatis*, the three fragments tested (900 bp, 1200 bp, and 3200 bp) reacted only with TWAR.

As noted above, the sensitivity of the DNA probes may be improved through (a) the use of single-strand probe; and (b) the isolation of ribosomal rRNA genes.

Development of Single-Stranded Probes.

Because double-stranded DNA probes hybridize less efficiently due to reannealing of the probe on itself, the concentration of probe available for hybridization is decreased. Thus, one can increase probe sensitivity by using a single-stranded probe in hybridizations. The major limitation to this method is the labeling of the single strand to a high enough specific activity. This problem can be circumvented by employing conditions that result in a double-stranded vector containing a single-stranded insert of the DNA probe (Artand, "Preparation of Nucleic Acid Probes," in *Nucleic Acid Hybridization: A Practical Approach*, pp. 17–45, Oxford Press, Oxford, England, 1985). The initial construction of a TWAR gene bank in the pUC vector facilitates subcloning into the replicative form (RF) of the single-stranded bacteriophage M13mp1S, since these vectors share the same lacZ/multiple cloning sites. The M13 "even" phage vectors (e.g., M13mp18) are recommended for use instead of the odd series (e.g., M13mp19) to prevent production of labeled probe that would hybridize to pBR322-derived sequences (ibid.). This single-stranded DNA probe may be prepared by the methods of Hu and Messing (Gene 17: 271–277, 1983). To radioactively label this probe, a commercially available universal probe primer can be used. This primer directs the synthesis of the vector DNA, and in the presence of a limited concentration of the radioactive precursor, the primer extension results in a double-stranded vector (M13) containing a single-stranded DNA probe insert. All protocol for isolation of the RF form of M13mp bacteriophage, subcloning, for pUC into M13, of recombinants, and selective synthesis (and labeling) of M13 sequences may be done by standard methods, as described by Messing (*Meth. Enzymol.* 101: 20–79, 1983). When this probe is used in Southern hybridization, it is not denatured prior to hybridization.

Isolation of Ribosomal RNA Genes.

An alternative method for increasing DNA probe sensitivity is to use a DNA probe that recognizes a multicopy sequence. The use of cloned DNA specific for ribosomal RNA is well documented as a means for increasing detection up to 1000-fold due to the large numbers of target molecules (ribosomes) per cell (Edelstein, *J. Clin. Microbiol.* 22: 425–427, 1986; Kingsbury, *Rapid Detection and Identification of Infectious Agents*, pp. 91–95, Academic Press, N.Y., 1985; Palmer and Falkow, *Microbiology* 1986, pp. 91–95, American Society for Microbiology, Washington, D.C., 1986). One such method is described below.

Total RNA is isolated from TWAR cultures at various times after infection for determination of the optimal time post-inoculation for isolation of 16s rRNA. rRNA may be isolated by the method of Kirby et al. with minor modifications (Kirby et al., Bioch. J. 104: 258–262, 1967; Johnson, *Methods in Microbiology* 18: 33–71, 1986). This protocol results in the isolation of bacterial rRNA that is essentially free of DNA, mRNA, and contains very little tRNA (Johnson, ibid.). To render buffers RNase free, diethyl pyrocarbonate (0.2%) is added to aqueous solutions for 1 hour and subsequently autoclaved. Glassware may be rendered RNase free by baking in a dry heat oven. Purified particles are harvested by centrifugation, sus pendad in $dH_2O$, and 10% napthalene disulphonate and 75 $\mu$l diethyl pyrocarbonate added. Cells are disrupted by passage through a French pressure cell into a mixture of phenol-cresol and 0.5% naphthalene disulphonate. Following shaking, the mixture is centrifuged at 17,000×G for 10 minutes, and the aqueous layer saved. Ten ml 20×SSC is added and SDS to a final concentration of 0.1% followed by another phenol-cresol extraction. RNA is precipitated by the addition of two volumes ethanol and pelleted by centrifugation. For further extraction of residual DNA, mRNA, and tRNA, cold 3M sodium acetate is added, the mixture homogenized, centrifuged, and re-precipitated. 5s, 16s and 23s ribosomal RNA is purified by electroelution from 1.5% agarose gels, as described by Griefson (*Gel Electrophoresis of Nucleic Acids*, pp. 1–139, IRL Press, Oxford, 1982). RNA is subjected to mild alkaline hydrolysis by heating in 50 mM Tris-HCl, with the time and temperature of incubation varying depending on the RNA species (Maizels, *Cell* 9: 431–438, 1976). This hydrolysis step frees 5' hydroxyl groups to make them available as substrates for polynucleotide kinase. rRNA is end-labeled with $^{32}p$ ATP with T4 polynucleotide kinase by standard protocol (Maniatis, ibid-). Each species may be used as probes of Southern hybridizations of TWAR adjusted with various restriction rRNA genes because most bacterial species contain more than one gene copy of rRNA sequences. The cloned TWAR rRNA genes are tested for their sensitivity in TWAR detection and their reactivity with *C. trachomatis* and *C. psittaci*. Depending on the Southern hybridization data, either restriction fragments thought to contain entire genes are electroeluted from agarose gels and cloned into similarly digested pUC18, or previously constructed gens banks are screened using the different rRNA species as probes. Depending on the fragment size containing the TWAR 16s rRNA gene, the gene is either directly subcloned or digested into smaller fragments and subcloned into M13mp18 and M13mp19 for DNA sequencing in both directions. All DNA sequencing may be done by the dideoxynucleotide chain terminator method by standard protocol (Sanger et al., *Proc. Natl. Acad. Sci.* 74: 5463–5467, 1977) using the commercially available kit from BRL. The cloned TWAR rRNA genes may be tested for their sensitivity in TWAR detection and their reactivity with *C. trachomatis* and *C. psittaci.*

From the foregoing it will be appreciated that, although specific embodiments of .the invention have been described herein for purposes of illustration, various modifications may be made without deviating from the spirit and scope of the invention. Accordingly, the invention iS not limited except as by the appended claims.

We claim:

1. An isolated oligonucleotide probe that specifically hybridizes to the DNA or rRNA of the TWAR organism and not to *C. trachomatis* or *C. psittaci.*

2. The oligonucleotide probe of claim 1 wherein said probe is a whole chromosomal DNA probe or a DNA fragment probe derived from the TWAR organism.

3. A method for detecting the presence of the TWAR organism in a biological sample, comprising:
   treating a biological sample suspected of containing the TWAR organism to isolate the DNA associated with the sample;
   affixing the isolated DNA to a substrate;
   incubating the substrate bearing the affixed DNA with an isolated labeled DNA probe capable of specifically hybridizing to at least a portion of the DNA sequence of the TWAR organism and not that of *C. trachomatis* or *C. psittaci*;
   separating non-hybridized probe from the substrate; and
   detecting the amount of label associated with DNA bound to the substrate, and therefrom determining the presence or absence of the TWAR organism.

4. The DNA probe of claim 3 wherein said probe is a whole chromosomal DNA probe or a DNA fragment probe derived from the TWAR organism.

5. A method for detecting the presence of the TWAR organism in a biological sample, comprising:
   affixing a biological sample suspected of containing the TWAR organism to a substrate;
   treating the substrate bearing the affixed sample to expose the DNA associated with the sample;
   incubating the substrate bearing DNA with an isolated labeled DNA probe capable of specifically hybridizing to at least a portion of the DNA sequence of the TWAR organism and not that of *C. trachomatis* or *C. psittaci*;
   separating non-hybridized probe from the substrate; and
   detecting the amount of label associated with DNA bound to the substrate, and therefrom determining the presence or absence of the TWAR organism.

6. The method of claim 5 wherein said probe is a whole chromosomal DNA probe or a DNA fragment probe derived from the TWAR organism.

7. The oligonucleotide probe of claim 1 which is labeled with a detectable marker.

8. A method for detecting the presence of the TWAR organism in a biological sample, comprising:
   treating a biological sample suspected of containing the TWAR organism to release DNA in the sample;
   incubating the DNA of the treated sample with an isolated oligonucleotide molecule capable of specifically hybridizing to at least a portion of the DNA sequence of the TWAR organism and not that of *C. trachomatis* or *C. psittaci*; and
   detecting a label associated with an isolated oligonucleotide molecule capable of specifically hydridizing to at least a portion of the DNA sequence of the TWAR organism and not that of *C. trachomatis* or *C. psittaci*, and thereby determining the presence or absence of the TWAR organism in the sample.

9. A method for detecting the presence of the TWAR organism in a biological sample, comprising:
   treating a biological sample suspected of containing the TWAR organism to release nucleic acids from cellular material in the sample;
   incubating rRNA of the treated sample with a isolated oligonucleotide molecule capable of specifically hybridizing to the rRNA of the TWAR organism and not to the rRNA of *C. trachomatis* or *C. psittaci*; and
   detecting any hybridization between the isolated oligonucleotide molecule and the isolated rRNA, thereby determining the presence or absence of TWAR organism in the sample.

* * * * *